(12) United States Patent
Samain et al.

(10) Patent No.: US 11,253,437 B2
(45) Date of Patent: Feb. 22, 2022

(54) OXIDATION DYEING PROCESS USING A SUBSTRATE BEARING AT LEAST ONE OXIDATION DYE, SEVERAL PRESERVATIVES AND AN OXIDIZING AQUEOUS COMPOSITION

(71) Applicant: L'OREAL, Paris (FR)

(72) Inventors: Henri Samain, Chevilly-Larue (FR); Cédric Trouche, Saint-Aunes (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 16/958,334

(22) PCT Filed: Dec. 21, 2018

(86) PCT No.: PCT/EP2018/086540
§ 371 (c)(1),
(2) Date: Jun. 26, 2020

(87) PCT Pub. No.: WO2019/129697
PCT Pub. Date: Jul. 4, 2019

(65) Prior Publication Data
US 2021/0059907 A1 Mar. 4, 2021

(30) Foreign Application Priority Data
Dec. 28, 2017 (FR) ...................... 1763319

(51) Int. Cl.
| | | |
|---|---|---|
| *A61Q 5/10* | (2006.01) | |
| *A61K 8/02* | (2006.01) | |
| *A45D 19/00* | (2006.01) | |
| *A61K 8/41* | (2006.01) | |
| *A61K 8/46* | (2006.01) | |
| *A61K 8/49* | (2006.01) | |
| *A45D 7/00* | (2006.01) | |

(52) U.S. Cl.
CPC .......... *A61K 8/0204* (2013.01); *A45D 19/018* (2021.01); *A61K 8/411* (2013.01); *A61K 8/46* (2013.01); *A61K 8/4973* (2013.01); *A61Q 5/10* (2013.01); *A45D 19/0075* (2021.01); *A45D 2007/001* (2013.01); *A61K 2800/10* (2013.01); *A61K 2800/262* (2013.01); *A61K 2800/4324* (2013.01); *A61K 2800/87* (2013.01)

(58) Field of Classification Search
CPC . A61Q 5/10; A61K 8/22; A61K 8/411; A61K 2800/4324; A61K 8/46; A61K 8/676; A61K 2800/262; A61K 8/4973; A61K 2800/10; A61K 2800/87; A45D 19/0075; A45D 2007/001

USPC ........................................................... 8/405
See application file for complete search history.

(56) References Cited

U.S. PATENT DOCUMENTS

| | | | |
|---|---|---|---|
| 8,920,521 B1 | 12/2014 | Benn | |
| 2005/0055782 A1* | 3/2005 | Rollat-Corvol | A61K 8/72 8/405 |
| 2005/0251928 A1* | 11/2005 | Kravtchenko | A61Q 5/08 8/405 |
| 2006/0230546 A1* | 10/2006 | Bone | A61Q 5/10 8/405 |
| 2012/0183483 A1* | 7/2012 | Misu | A61K 8/345 424/70.2 |
| 2016/0317399 A1* | 11/2016 | Samain | B44C 1/165 |

FOREIGN PATENT DOCUMENTS

| | | |
|---|---|---|
| EP | 1321134 A2 | 6/2003 |
| EP | 1695689 A1 | 8/2006 |
| FR | 3015895 A1 | 7/2015 |
| JP | 2005041820 A | 2/2005 |

OTHER PUBLICATIONS

International Search Report dated Mar. 25, 2019, issued in corresponding International Application No. PCT/EP2018/086540, filed Dec. 21, 2018, 3 pages.
Database WPI, Week 200517, Thomson Scientific, London, Great Britain, AN 2005-156855 and JP2005-041820, Feb. 17, 2005.
Notice of Reasons for Rejection dated Jul. 5, 2021, issued in corresponding JP Application No. 2020-536211, filed Dec. 10, 2020, 10 pages.

* cited by examiner

*Primary Examiner* — Eisa B Elhilo
(74) *Attorney, Agent, or Firm* — Christensen O'Connor Johnson Kindness PLLC

(57) ABSTRACT

Oxidation dyeing process using a substrate bearing at least one oxidation dye, several preservatives and an oxidizing aqueous composition The present invention relates to a process for the oxidation dyeing of keratin fibres, in particular human keratin fibres such as the hair, comprising a step of application, to said keratin fibres, i) of a substrate comprising on its surface one or more oxidation dyes, one or more thiolated reducing agents and one or more organic reducing agents of reductone type, and a step of application, to said keratin fibres, ii) of an oxidizing aqueous composition comprising one or more oxidizing agents. The present invention also relates to a process for preparing said substrate. The invention also relates to an element in sheet form, pretreated by a composition comprising one or more oxidation dyes, one or more thiolated reducing agents, and one or more organic reducing agents of reductone type.

30 Claims, No Drawings

OXIDATION DYEING PROCESS USING A SUBSTRATE BEARING AT LEAST ONE OXIDATION DYE, SEVERAL PRESERVATIVES AND AN OXIDIZING AQUEOUS COMPOSITION

The present invention relates to a process for the oxidation dyeing of keratin fibres, in particular human keratin fibres such as the hair, comprising a step of application, to said keratin fibres, i) of a substrate comprising on its surface one or more oxidation dyes, one or more thiolated reducing agents and one or more organic reducing agents of reductone type, and a step of application, to said keratin fibres, ii) of an oxidizing aqueous composition comprising one or more oxidizing agents.

The present invention also relates to a process for preparing said substrate.

The invention also relates to an element in sheet form, pretreated by a composition comprising one or more oxidation dyes, one or more thiolated reducing agents, and one or more organic reducing agents of reductone type.

Standard oxidation dyeing processes consist generally in applying, to keratin fibres, a dye composition comprising oxidation bases or a mixture of oxidation bases and couplers with hydrogen peroxide ($H_2O_2$ or aqueous hydrogen peroxide solution), as oxidizing agent, in leaving it to diffuse, and then in rinsing said fibres. The colourings resulting therefrom are generally permanent, vivid and resistant to external agents, especially to light, bad weather, washing, perspiration and rubbing.

However, it has been found that it is often difficult or even impossible to obtain colourings with novel visual results by means of the "standard" oxidation dyeing techniques. In particular, these processes do not make it possible to satisfactorily obtain coloured patterns, which may lead to novel optical effects on the entire head of hair and which are both sharp and precise.

These standard oxidation dyeing processes also have the drawback of staining the hands of the user or of the colourist during the application to the hair of the ready-to-use composition resulting from mixing the dye composition and the oxidizing composition. Similarly, this type of process may also give rise to undesirable stains on the user's scalp, contour of the face and/or clothing, which may be due to application errors and/or to problems of running of the compositions.

These standard oxidation dyeing processes also entail the risk of not leading to the final colouring desired by the user because of an error arising during the handling of the dye compositions and oxidizing compositions or because of a poor choice of the starting dye compositions.

It has also been found that the storage of the dye compositions and oxidizing compositions used for obtaining the desired colouring may pose problems of space occupation, especially in hairstyling salons.

These oxidation dyeing processes may thus prove to be impractical for achieving many varied colours as a function of the different users.

Moreover, it is already known from document FR 3 015 895 to carry out a dyeing process consisting in bringing keratin fibres into contact with a substrate pretreated with one or more oxidation dyes and an oxidizing aqueous composition. The oxidation dyes present on the surface of the substrate dissolve and react with the oxidizing agent, on contact with said fibres, to dye them, which leads to colourings that may be unified and/or to coloured patterns.

However, the dyeing processes described by this document are not entirely satisfactory in terms of preserving said substrates. Indeed, it has been noticed that the dyeing power of the oxidation dyes present on said substrates could greatly decrease in a few days by the effect of the atmospheric oxygen. However, it is highly common for the user to wait one or more months before using the dyeing product.

There is therefore a real need to implement a process for the oxidation dyeing of keratin fibres, in particular human keratin fibres such as the hair, consisting in bringing the keratin fibres into contact with a substrate pretreated with one or more oxidation dyes and an oxidizing aqueous composition with satisfactory preservation of said substrate; that is to say capable of retaining a potent dyeing power even when carrying out said process several weeks after said substrate is prepared.

It is also necessary for this process not to have the drawbacks mentioned previously, i.e. to especially be capable of leading, on said fibres, to colourings that may be unified and/or that may have novel visual results, in particular precise coloured patterns, of reducing the problems of space occupation of the compositions used, of minimizing the risks of contact that may arise between the compositions used and the user's hands, scalp and/or clothing, and also the risks of not obtaining the desired colouring.

This aim is achieved by the present invention, a subject of which is especially a process for the oxidation dyeing of keratin fibres, in particular human keratin fibres such as the hair, comprising:

i) a step of application, to said keratin fibres, of a substrate comprising a surface coated with at least one layer constituted of a dye composition comprising:
  one or more oxidation dyes;
  one or more thiolated reducing agents, and
  one or more organic reducing agents of reductone type; and ii) a step of application, to said keratin fibres, of an oxidizing aqueous composition comprising one or more chemical oxidizing agents;

it being understood that the total water content of said dye composition is less than 20% by weight relative to the total weight of the dye composition.

Thus, it has been observed, surprisingly, that the dyeing process made it possible to obtain intense colourations, even after carrying out the process several weeks after the substrate is prepared.

This is because the process uses a substrate which is readily preserved when it is brought into contact with atmospheric oxygen.

The process for dyeing keratin fibres therefore uses a substrate on which one or more oxidation dyes, one or more thiolated reducing agents, and one or more organic reducing agents of reductone type have been deposited. In other words, the substrate has been pretreated at the surface thereof by a dye preparation composition containing one or more oxidation dyes, one or more thiolated reducing agents, and one or more organic reducing agents of reductone type.

In particular, the dye composition is present at the surface of the substrate and may be localized in certain places of said surface so as to represent one or more geometrical forms in order thereafter to produce one or more coloured patterns on the keratin fibres after contact between said fibres, the pretreated substrate and the oxidizing aqueous composition. In other words, the substrate may be pretreated in places with a dye preparation composition containing one or more oxidation dyes, one or more thiolated reducing agents, and one or more organic reducing agents of reductone type so as to be able to produce one or more coloured patterns on the fibres.

The dyeing process according to the invention thus makes it possible to produce on the keratin fibres, with great precision, coloured patterns that are visually sharp. In particular, this process makes it possible to produce millimetre-sized coloured patterns having all types of forms, such as spots or waves, which are easily reproducible. These patterns may thus lead to novel optical effects when they are then repeated over the entire head of hair.

In other words, the dyeing process according to the invention makes it possible to obtain patterns, especially millimetre-sized patterns, homogeneously over the entire head of hair, or in a localized manner on a part of the head of hair. These patterns may be imaginative from an aesthetic viewpoint or may serve to hide an irregularity in the colour or appearance of the keratin fibres, especially in the case of regrowth or fading of the ends.

Moreover, by using substrates comprising one or more oxidation dyes, i.e. substrates that are pretreated with a composition containing such dyes, this process makes it possible to reduce the risks of staining on the user's hands, scalp, face and/or clothing. Specifically, this process makes it possible to avoid the problems of running and/or errors in application of the dye compositions and oxidizing compositions.

Similarly, by means of applying such pretreated substrates, this process makes it possible to reduce the problem of storage of the dye compositions and oxidizing compositions used in the standard processes, and consequently to reduce the problems of space occupation. In particular, the user may have at their disposal a larger number of substrates pretreated with oxidation dyes while at the same time saving space in hairstyling salons.

The oxidation dyeing process according to the invention also has the advantage of minimizing the risks of errors that may arise during the handling of the dye compositions and oxidizing compositions or in the choice of starting dye compositions so as to obtain the desired colouring.

The oxidation dyeing process according to the invention also makes it possible to obtain colourings and/or patterns whose colourings are vivid, sparingly selective and resistant with respect to external agents (such as shampoos, light, perspiration or bad weather).

In particular, the dyeing process according to the invention leads to the production of patterns whose colouring is vivid and resistant with respect to shampooing.

The present invention also relates to a process for producing a substrate as defined previously, comprising at least one step of deposition, on the surface of said substrate, of at least one dye preparation composition containing one or more oxidation dyes, one or more thiolated reducing agents, and one or more organic reducing agents of reductone type; and at least one step of drying said substrate.

The invention also relates to an element in sheet form, pretreated at the surface thereof by a dye preparation composition comprising one or more oxidation dyes, one or more thiolated reducing agents, and one or more organic reducing agents of reductone type.

In other words, another subject of the present invention relates to an element in sheet form comprising a surface coated with at least one layer constituted of a dye composition comprising one or more oxidation dyes, one or more thiolated reducing agents, and one or more organic reducing agents of reductone type.

In particular, the element in sheet form comprises one or more oxidation dyes, one or more thiolated reducing agents, and one or more organic reducing agents of reductone type which have been deposited at the surface thereof.

The element in sheet form according to the invention has the advantage of being easy to apply to locks of hair. In particular, such an element may be positioned with a high level of precision at the place where it is desired to produce the coloured pattern(s) on the locks of hair.

The element in sheet form has the advantage of being able to be easily stored in the user's home when compared with the use of dye compositions used in standard oxidation dyeing processes, thereby making it possible to substantially reduce the space occupation.

Moreover, the element in sheet form may be prepared directly in the hairstyling salon or beforehand.

Other subjects, characteristics, aspects and advantages of the invention will emerge even more clearly on reading the description and the examples that follow.

For the purposes of the present invention and unless otherwise indicated:

a "heteroaryl radical" represents a fused or non-fused, optionally cationic, 5- to 22-membered monocyclic or polycyclic group, comprising from 1 to 6 heteroatoms chosen from nitrogen, oxygen, sulfur and selenium atoms, and at least one ring of which is aromatic; preferentially, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridyl, tetrazolyl, dihydrothiazolyl, imidazopyridyl, imidazolyl, indolyl, isoquinolyl, naphthoimidazolyl, naphthooxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridyl, thiazoylimidazolyl, thiopyrylyl, triazolyl, xanthinyl or thioxanthinyl;

an "aryl" radical represents a fused or non-fused, monocyclic or polycyclic carbon-based group, comprising from 6 to 22 carbon atoms, at least one ring of which is aromatic; preferentially, the aryl radical is a phenyl, biphenyl, naphthyl, indenyl, anthracenyl or tetrahydronaphthyl;

the "aryl" or "heteroaryl" radicals or the aryl or heteroaryl part of a radical may be substituted with at least one substituent borne by a carbon atom, chosen from:

a $C_1$-$C_6$ and preferably $C_1$-$C_4$ alkyl radical optionally substituted with one or more radicals chosen from the radicals hydroxyl, $C_1$-$C_2$ alkoxy, $C_2$-$C_4$ (poly)hydroxyalkoxy, acylamino, amino substituted with two $C_1$-$C_4$ alkyl radicals, which may be identical or different, optionally bearing at least one hydroxyl group, or the two radicals possibly forming, with the nitrogen atom to which they are attached, a saturated or unsaturated, optionally substituted 5- to 7-membered and preferably 5- or 6-membered heterocycle optionally comprising another nitrogen or non-nitrogen heteroatom;

a halogen atom;

a hydroxyl or thiol group;

a $C_1$-$C_6$ alkoxy or $C_1$-$C_6$ alkylthio radical;

a (poly)hydroxy($C_2$-$C_6$)alkoxy radical;

an amino radical;

a 5- or 6-membered heterocycloalkyl radical, preferentially morpholino, piperazino, piperidino or pyrolidino, which is optionally substituted with a ($C_1$-$C_4$) alkyl radical, preferentially methyl;

a 5- or 6-membered heteroaryl radical, preferentially imidazolyl, optionally substituted with a ($C_1$-$C_4$) alkyl radical, preferentially methyl;

an amino radical substituted with one or two identical or different $C_1$-$C_6$ alkyl radicals, optionally bearing at least:
- a hydroxyl group,
- an amino group optionally substituted with one or two optionally substituted $C_1$-$C_3$ alkyl radicals, said alkyl radicals possibly forming, with the nitrogen atom to which they are attached, a saturated or unsaturated, optionally substituted 5- to 7-membered heterocycle, optionally comprising at least one other nitrogen or non-nitrogen heteroatom,
- a quaternary ammonium group —$N^+R'R''R'''$, $M^-$ for which R', R" and R''', which may be identical or different, represent a hydrogen atom or a $C_1$-$C_4$ alkyl group and $M^-$ represents an anionic counterion,
- or an optionally cationic 5- or 6-membered heteroaryl radical, preferentially imidazolium, optionally substituted with a ($C_1$-$C_4$)alkyl radical, preferentially methyl;

an acylamino radical (—N(R)—C(O)—R') in which the R radical is a hydrogen atom or a $C_1$-$C_4$ alkyl radical optionally bearing at least one hydroxyl group and the R' radical is a $C_1$-$C_2$ alkyl radical;

a carbamoyl radical (($R)_2$N—C(O)—) in which the R radicals, which may be identical or different, represent a hydrogen atom or a $C_1$-$C_4$ alkyl radical optionally bearing at least one hydroxyl group;

an alkylsulfonylamino radical (R'—S(O)$_2$—N(R)—) in which the R radical represents a hydrogen atom or a $C_1$-$C_4$ alkyl radical optionally bearing at least one hydroxyl group and the R' radical represents a $C_1$-$C_4$ alkyl radical, or a phenyl radical;

an aminosulfonyl radical (($R)_2$N—S(O)$_2$—) in which the R radicals, which may be identical or different, represent a hydrogen atom or a $C_1$-$C_4$ alkyl radical optionally bearing at least one hydroxyl group;

a carboxyl radical in the acid or salified form (preferably salified with an alkali metal or a substituted or unsubstituted ammonium);

a cyano group;

a nitro or nitroso group;

a polyhaloalkyl group, preferably trifluoromethyl;

a cyclic or heterocyclic radical, or a non-aromatic part of an aryl or heteroaryl radical, may also be substituted with one or more oxo groups;

an "alkyl radical" is a linear or branched $C_1$-$C_{10}$, in particular $C_1$-$C_8$, more particularly $C_1$-$C_6$ and preferably $C_1$-$C_4$ hydrocarbon-based radical;

the limits of a range of values are included in that range, in particular in the expressions "between . . . and . . . " and "ranging from . . . to . . . ";

the expression "at least one" is equivalent to the expression "one or more" and can be replaced therewith.

Dyeing Process

As indicated previously, the oxidation dyeing process uses, on said keratin fibres, a substrate comprising a surface coated with at least one layer constituted of a dye composition comprising one or more oxidation dyes, one or more thiolated reducing agents, and one or more organic reducing agents of reductone type.

The substrate may be in the form of an element in sheet form or in another embodiment.

According to a preferred embodiment, the substrate is an element in sheet form.

The element in sheet form may be made of plastic material, in particular thermoplastic, paper, metal, especially aluminium, a woven, a nonwoven of non-absorbent fibres, especially of cellulose or a derivative thereof, or polyamide 6,6.

Preferably, the element in sheet form is a sheet of plastic material, especially of thermoplastic, or a nonwoven material of non-absorbent fibres, especially a nonwoven based on cellulose or a derivative thereof.

In particular, the element in sheet form used in the dyeing process is a plastic sheet.

The element in sheet form may consist of a water-soluble material, which makes it possible, for example, to remove it by washing the hair.

Preferably, the element in sheet form comprises an assembly of a layer of a water-soluble material and a layer of a non-water-soluble material, for example an aluminium foil.

The substrate may be designed to be able to be closed around a lock of hair. In this case, such a substrate is, for example, provided with a fastening means for keeping it in such a state, for example an adhesive disposed close to one edge or a mechanical attachment relief.

Preferably, the element in sheet form has a basis weight ranging from 20 to 300 g/m$^2$ and even more preferentially ranging from 30 to 200 g/m$^2$.

The element in sheet form especially has a thickness ranging from 40 to 1000 micrometres, preferably a thickness ranging from 40 to 400 micrometres and better still from 60 to 200 micrometres.

The element in sheet form may be opaque or transparent. Preferably, the element in sheet form is transparent, which facilitates its positioning on the hair, especially when it is desired to produce one or more patterns at a precise place on the lock or on the head of hair. In other words, the transparency of the element in sheet form facilitates the implementation of the dyeing process, especially in the production of coloured patterns, and improves its precision.

The element in sheet form used in the dyeing process according to the invention is preferably flexible and strong. Preferentially, the strength of the sheet is greater than 300 kPa (standard TAPPI-T403).

Preferably, the element in sheet form is water-resistant. In particular, the water absorption of said element is measured by the COBB 60 test which corresponds to the capacity of said element to absorb water during contact for 60 seconds (the procedure of which is given by standard ISO 535, TAPPI-T411 measurement).

Thus, the element in sheet form absorbs less than 100 g/m$^2$ and preferentially less than 40 g/m$^2$ of water.

Preferably, the element in sheet form is resistant to oily compounds. Thus, use may be made of a "food" paper, i.e. a complex of paper and of polymeric compound of the polyethylene type or of paper and paraffin, which is capable of acting as a barrier to water and to oils.

The element in sheet form may optionally be covered with a deposit of an adhesive composition. This adhesive layer makes it possible to improve the adhesion of the oxidation dye(s) to the surface of the element in sheet form.

According to a preferred embodiment, the element in sheet form comprising a surface coated with at least one layer constituted of a dye composition comprising one or more oxidation dyes, one or more thiolated reducing agents, and one or more organic reducing agents of reductone type may be covered with a protection means which serves to protect the surface of said element from external elements. Thus, the element in sheet form comprises, at the surface thereof, one or more oxidation dyes, one or more thiolated reducing agents, and one or more organic reducing agents of reductone type which may be covered with a protective layer. Such a protective layer makes it possible to further minimize the impairment of the oxidation dye(s) caused by moisture, light or atmospheric oxygen.

Thus, the element in sheet form may be protected by implementing processes used in paper varnishing techniques (oil varnish, acrylic varnish, etc.), and in particular by using a water-based or organic acrylic varnish composition.

In this way, the element in sheet form comprising a surface coated with at least one layer constituted of a dye composition comprising one or more oxidation dyes, one or more thiolated reducing agents, and one or more organic reducing agents of reductone type may be protected at the surface with a layer of acrylic varnish.

In other words, the element in sheet form comprises, at the surface thereof, at least one layer constituted of a dye composition containing one or more oxidation dyes, one or more thiolated reducing agents, and one or more organic reducing agents of reductone type, and a layer of acrylic varnish, the two layers being juxtaposed one over the other.

The mass per unit area of the layer of acrylic varnish ranges from 1 to 10 g/m$^2$ and more particularly from 2 to 5 g/m$^2$.

According to one variant, the element in sheet form is covered with a detachable protective sheet. For this purpose, the edges of the element in sheet form and of the protective sheet are bonded together by means of a fastening means, especially an adhesive, which may be produced via any type of method, especially by heat sealing. Thus, good cohesion is ensured between the protective sheet and the element in sheet form.

Advantageously, the protective sheet is UV-opaque to ensure better protection.

According to another variant, the element in sheet form may be covered by another protective means, namely a hermetic wrapping, defining above the element a space without oxygen (under vacuum or under an inert atmosphere).

As indicated previously, the substrate comprises a surface coated with at least one layer constituted of a dye composition also comprising one or more oxidation dyes.

The oxidation dyes may be chosen from one or more oxidation bases, optionally in combination with one or more couplers. Preferably, the oxidation dyes comprise at least one oxidation base and at least one coupler.

By way of example, the oxidation bases are chosen from para-phenylenediamines, bisphenylalkylenediamines, para-aminophenols, ortho-aminophenols and heterocyclic bases, and addition salts thereof.

Among the para-phenylenediamines, examples that may be mentioned include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N—(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N—(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N—(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl) pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bisphenylalkylenediamines, examples that may be mentioned include N,N'-bis(β-hydroxyethyl)-N,N'-bis(4'-aminophenyl)1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,6-dioxaoctane and the addition salts thereof.

Among the para-aminophenols, examples that may be mentioned include para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols, examples that may be mentioned include 2-aminophenol, 2-amino-5-methylphenol, 2-amino-6-methylphenol and 5-acetamido-2-aminophenol, and addition salts thereof.

Among the heterocyclic bases, examples that may be mentioned include pyridine derivatives, pyrimidine derivatives and pyrazole derivatives.

Among the pyridine derivatives, mention may be made of the compounds described for example in patents GB 1 026 978 and GB 1 153 196, for instance 2,5-diaminopyridine, 2-(4-methoxyphenyl)amino-3-aminopyridine and 3,4-diaminopyridine, and addition salts thereof.

Other pyridine oxidation bases that are useful in the present invention are the 3-aminopyrazolo[1,5-a]pyridine oxidation bases or addition salts thereof described, for example, in patent application FR 2 801 308. Examples that may be mentioned include pyrazolo[1,5-a]pyrid-3-ylamine, 2-(acetylamino)pyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl) methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1, 5-a]pyridine, 3,4-diaminopyrazolo[1,5-a]pyridine, pyrazolo

[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol and the addition salts thereof.

Among the pyrimidine derivatives, mention may be made of the compounds described, for example, in patents DE 2359399, JP 88-169571, JP 05-63124 and EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof, and the tautomeric forms thereof, when a tautomeric equilibrium exists.

Among the pyrazole derivatives, mention may be made of the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-amino ethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof. Use may also be made of 4,5-diamino-1-(β-methoxyethyl)pyrazole.

A 4,5-diaminopyrazole will preferably be used, and even more preferentially 4,5-diamino-1-(β-hydroxyethyl)pyrazole and/or a salt thereof.

Pyrazole derivatives that may also be mentioned include diamino-N,N-dihydropyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a salt thereof.

Heterocyclic bases that will preferentially be used include 4,5-diamino-1-(β-hydroxyethyl)pyrazole and/or 2,3-diamino-6,7-dihydro-1H,5H-pyrazolo[1,2-a]pyrazol-1-one and/or a salt thereof.

Preferably, the oxidation bases are chosen from para-phenylenediamine, 1-methyl-2,5-diaminobenzene, para-aminophenol, 1-hydroxyethyl-4,5-diaminopyrazole sulfate and 2,3-diaminodihydroxypyrazolone dimethosulfonate, and the addition salts thereof, and mixtures thereof.

The coupler(s) are advantageously chosen from those conventionally used for the dyeing of keratin fibres.

Among these couplers, mention may be made especially of meta-phenylenediamines, meta-aminophenols, meta-diphenols, naphthalene-based couplers and heterocyclic couplers, and also the addition salts thereof.

Examples that may be mentioned include 2-methyl-5-aminophenol, 5-N—(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N—(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the invention are especially chosen from the addition salts with an acid, such as hydrochlorides, hydrobromides, sulfates, citrates, succinates, tartrates, lactates, tosylates, benzenesulfonates, phosphates and acetates.

Preferably, the coupler(s) are chosen from resorcinol, 2-methylresorcinol, 5-N—(β-hydroxyethyl)amino-2-methylphenol, 2-methyl-5-aminophenol, 1-β-hydroxyethyloxy-2,4-diaminobenzene dihydrochloride, 3-aminophenol, (5-N-hydroxyethyl)amino-o-cresol, 5-amino-ortho-cresol and 1-β-hydroxyethyloxy-2,4-diaminobenzene dihydrochloride, the addition salts thereof, and mixtures thereof.

As indicated previously, the substrate comprises a surface coated with at least one layer constituted of a dye composition also comprising one or more thiolated reducing agents.

The thiolated reducing agent(s) may be chosen from organic compounds comprising one or more mercapto (—SH) groups and preferably at least one other function chosen from carboxylic acid, amine, amide, ester and alcohol functions and mixtures thereof.

According to a preferred embodiment of the invention, the thiolated reducing agent(s) used according to the invention are chosen from those of formulae i-1 and also the organic or mineral acid or base salts thereof, optical isomers thereof and tautomers thereof, and the solvates such as hydrates; and/or mixtures thereof:

R—SH      i-1 in which formula i-1:
R represents:
- a linear or branched $(C_1-C_8)$alkyl, preferably $(C_1-C_6)$ alkyl, group which is optionally substituted, preferably substituted with one or more groups chosen from carboxy C(O)OH, (di)$(C_1-C_4)$(alkyl)amino, hydroxyl —OH, thiol —SH; and/or optionally interrupted with one or more heteroatoms or groups chosen from —O—, —S—, —N(R''')—, C(O) or combinations thereof such as —O—C(O)—, —C(O)—O—, —N(R''')—C(O)—, or —C(O)—N(R''')—; with R''' representing a hydrogen atom or a $(C_1-C_6)$alkyl group, preferably a $(C_1-C_4)$ alkyl group; or
- a (hetero)aryl group optionally substituted especially with one or more hydroxyl, thiol or carboxy groups.

According to a particular embodiment of the invention, the thiolated reducing agent(s) are chosen from those of formula i-1 as defined previously, and also the organic or mineral acid or base salts thereof, optical isomers thereof and tautomers thereof, and the solvates such as hydrates; and/or the mixtures thereof, for which R represents a linear or branched $(C_1-C_8)$alkyl, preferentially $(C_1-C_6)$alkyl, group,
- which is substituted with one or more groups chosen from carboxy C(O)OH, amino, hydroxyl —OH and thiol —SH; and/or
- which is optionally interrupted with one or more heteroatoms or groups chosen from —O—, —N(R''')—, C(O) or combinations thereof such as —O—C(O)—, —C(O)—O—, —N(R''')—C(O)—, or —C(O)—N(R''')—, with R''' representing a hydrogen atom or a $(C_1-C_6)$alkyl group, preferentially a $(C_1-C_4)$alkyl group.

More preferentially, R represents a linear or branched, non-interrupted $(C_1-C_8)$alkyl group, better still $(C_1-C_6)$alkyl group.

According to another particular embodiment of the invention, the thiolated reducing agent(s) are chosen from those of formula i-1 as defined previously, and also the organic or mineral acid or base salts thereof, optical isomers thereof and tautomers thereof, and the solvates such as hydrates; and/or the mixtures thereof, for which R represents:
- a phenyl group optionally substituted with one or more hydroxyl, thiol or carboxy groups; or
- a 5- to 10-membered, preferably 9- or 10-membered bicyclic, heteroaryl, comprising from 1 to 4 heteroatoms chosen from O, S or N, preferably N, optionally substituted with one or more hydroxyl or thiol groups.

Preferably, the thiolated reducing agent(s) are chosen from thioglycolic acid, thio lactic acid, cysteine, cysteamine, homocysteine, glutathione, thioglycerol, thiomalic acid, 2-mercaptopropionic acid, 3-mercaptopropionic acid, thiodiglycol, 2-mercaptoethanol, dithiothreitol, N-acetylcysteine, esters and amides of thioglycolic or thiolactic acids, especially glyceryl monothioglycolate; and also the organic or mineral acid or base salts thereof, optical isomers thereof, tautomers thereof, and the solvates such as hydrates; and mixtures of these compounds.

Preferentially, the thiolated reducing agent(s) are chosen from thioglycolic acid, thiolactic acid, cysteamine, and also the organic or mineral acid or base salts thereof, optical isomers thereof and tautomers thereof, and the solvates such as hydrates, and mixtures thereof. More preferentially still, the thiolated reducing agent(s) are chosen from thioglycolic acid, thio lactic acid, and mixtures thereof.

As indicated previously, the thiolated reducing agent(s) may be used especially in the form of salts, in particular alkali metal salts such as sodium and potassium salts, alkaline-earth metal salts, for example magnesium and calcium salts, ammonium salts, amine salts and amino alcohol salts. Ammonium thioglycolate may thus be used as thiol.

As indicated previously, the substrate comprises a surface coated with at least one layer constituted of a dye composition also comprising one or more organic reducing agents of reductone type.

As is known per se, the term "reductone" denotes a compound comprising an enediol structure —(HO)C=C(OH)— adjacent to a carbonyl group —C(O)—.

Thus, the organic reducing agent(s) of reductone type used according to the present invention are preferably of general formula (IX) and also the salts thereof; and/or the mixtures thereof:

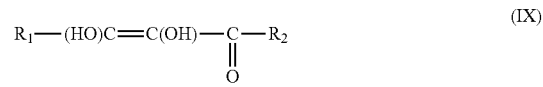

in which formula
$R_1$ and $R_2$ independently of one another each denote a group containing at least one carbon and/or oxygen atom, $R_1$ and $R_2$ possibly forming with the three carbon atoms of the compound of formula (IX) a ring, which is preferably 5- or 6-membered, the additional constituent atoms of which are constituted of carbon and/or oxygen atoms.

Preferably, $R_1$ and $R_2$ form with the three carbon atoms of the compound of formula (IX) a 5-membered ring, the additional constituent atoms of which are constituted of carbon and/or oxygen atoms.

As indicated previously, the organic reducing agent(s) of reductone type of formula (IX) may be in acid form, or in the form of salts, especially in the form of salts of alkali metals such as sodium and potassium, or salts of alkaline-earth metals such as calcium and magnesium, or in the form of esters, especially of $C_8$ to $C_{30}$ fatty acids.

Preferentially, the organic reducing agent(s) of reductone type of formula (IX) are lactones.

According to a preferred embodiment of the invention, the organic reducing agent(s) of reductone type are chosen from reductic acid, ascorbic acid, erythorbic acid or isoascorbic acid, and also salts thereof such as sodium or potassium salts, ascorbyl palmitate, and/or mixtures thereof.

More preferentially, the organic reducing agent(s) of reductone type are chosen from ascorbic acid, erythorbic acid, and the salts of these compounds, especially the sodium or potassium salts.

According to a particular embodiment of the invention, the weight ratio of the total content by weight of the thiolated reducing agent(s) and the organic reducing agent(s) of reductone type present in the dye composition to the total content by weight of the oxidation dye(s) present in the dye composition is between 0.05 and 40, preferably between 0.1 and 30, preferentially between 0.2 and 30.

The dye composition may cover all or part of the surface of the substrate. Thus, the surface of the substrate may be entirely or partially covered with a layer or several layers constituted of the dye composition.

Preferably, the dye preparation composition is deposited on part of the surface of the substrate and represents patterns, which, after contact with the keratin fibres and the oxidizing aqueous composition, will make it possible to produce the coloured patterns on said fibres. In other words, the oxidation dye(s) are deposited in the form of patterns on the surface of the substrate. Thus, the surface of the substrate comprises one or more layers constituted of the dye composition arranged in one or more particular geometrical forms, known as patterns, which, after reaction with the oxidizing aqueous composition, lead to the production of coloured patterns on said fibres.

The pattern(s) may have any form, especially a geometrical form.

Thus, the dye composition comprising the oxidation dye(s), the thiolated reducing agent(s) and the organic reducing agent(s) of reductone type is present over part of the surface of the substrate and represents patterns having the desired form.

The substrate may comprise, on the face opposite the face bearing the oxidation dye(s), the thiolated reducing agent(s) and the organic reducing agent(s) of reductone type, a copy of the desired pattern(s). The production of these patterns on the opposite face makes it possible to indicate the place where the oxidation dye(s), the thiolated reducing agent(s) and the organic reducing agent(s) of reductone type may then be deposited on the surface of the substrate. Such a production facilitates thereafter the emplacement of the substrate on the keratin fibres at the place where it is desired to produce the pattern.

According to a preferred embodiment of the invention, the surface of the substrate comprises, prior to the deposition of the oxidation dye(s), the thiolated reducing agent(s) and the organic reducing agent(s) of reductone type, one or more patterns. In other words, the patterns that it is desired to obtain on the keratin fibres may be produced, for example printed, beforehand on the surface of the substrate intended to be pretreated.

According to another preferred embodiment of the invention, the substrate is transparent.

The substrate may optionally comprise a surface coated with at least one layer constituted of a dye composition also comprising one or more alkaline agents. In other words, the dye composition may optionally comprise one or more oxidation dyes, one or more thiolated reducing agents, one or more organic reducing agents of reductone type and one or more alkaline agents.

The alkaline agents may be chosen from carbonates, alkanolamines such as monoethanolamine, diethanolamine, triethanolamine and derivatives thereof, oxyethylenated and/or oxypropylenated ethylenediamines, mineral or organic hydroxides, alkali metal silicates such as sodium metasilicates, amino acids, preferably basic amino acids such as arginine, lysine, ornithine, citrulline and histidine, and the compounds of formula (I) below:

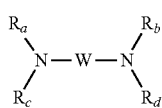

(I)

in which:
W is a divalent $(C_1-C_8)$alkylene group, preferably a propylene group, optionally substituted especially with a hydroxyl group or a $C_1-C_4$ alkyl radical;
$R_a$, $R_b$, $R_c$ and $R_d$, which may be identical or different, represent a hydrogen atom or a $C_1-C_4$ alkyl or $C_1-C_4$ hydroxyalkyl radical.

The mineral or organic hydroxides are preferably chosen from i) hydroxides of an alkali metal, ii) hydroxides of an alkaline-earth metal, for instance sodium hydroxide or potassium hydroxide, iii) hydroxides of a transition metal, such as hydroxides of metals from groups III, IV, V and VI, iv) hydroxides of lanthanides or actinides, quaternary ammonium hydroxides and guanidinium hydroxide.

The hydroxide may be formed in situ, for instance guanidine hydroxide, by reacting calcium hydroxide with guanidine carbonate.

In particular, the alkaline agents used are solid in the dry state.

In a first variant of the invention, the alkaline agents are solid before use in the dye preparation composition for treating the surface of the substrate, and are preferably chosen from carbonates, mineral hydroxides such as soluble sodium or potassium hydroxides or silicates.

In another variant of the invention, the alkaline agents are chosen from alkanolamines, in particular monoethanolamine, diethanolamine and triethanolamine.

The substrate may optionally comprise a surface coated with at least one layer constituted of a dye composition also comprising one or more additional antioxidant active agents, that are preferentially solid before being used in the dye preparation composition, chosen from sulfites, bisulfites such as ammonium bisulfites and alkali metal or alkaline-earth metal bisulfites such as, for example, sodium bisulfites, sulfinates.

Said dye composition may optionally also comprise one or more compounds capable of slowing down the oxidative condensation reaction, chosen from δ-gluconolactone, sodium gluconate, potassium gluconate, calcium gluconate, potassium bitartrate, sodium acetate, sorbitol, acids such as ethylenediaminetetraacetic acid (EDTA), citric acid, phosphoric acid, and tartaric acid.

Said dye composition may optionally also comprise one or more organic solvents.

Organic solvents that may be mentioned include linear or branched and preferably saturated monoalcohols or diols, comprising 2 to 6 carbon atoms, such as ethyl alcohol, isopropyl alcohol, hexylene glycol (2-methyl-2,4-pentanediol), neopentyl glycol and 3-methyl-1,5-pentanediol, butylene glycol, dipropylene glycol and propylene glycol; aromatic alcohols such as benzyl alcohol or phenylethyl alcohol; polyols containing more than two hydroxyl functions, such as glycerol; polyol ethers, for instance ethylene glycol or propylene glycol monomethyl, monoethyl or monobutyl ether; and also diethylene glycol alkyl ethers, especially $C_1-C_4$ alkyl ethers, for instance diethylene glycol monoethyl ether or monobutyl ether.

The substrate may optionally comprise a surface coated with at least one layer constituted of a dye composition also comprising one or more activators or catalysts. In particular, the substrate also comprises a layer of one or more metal salts in a content ranging from 1% to 20% by weight relative to the weight of the oxidation dyes present in the dye preparation composition before deposition on the surface of the substrate.

As indicated previously, the oxidation dyeing process uses an oxidizing aqueous composition containing one or more chemical oxidizing agents.

The term "chemical oxidizing agent" means an oxidizing agent other than atmospheric oxygen.

Preferably, the chemical oxidizing agent(s) are chosen from hydrogen peroxide, urea peroxide, alkali metal bromates or ferricyanides, peroxygenated salts, for instance alkali metal or alkaline-earth metal persulfates, perborates and percarbonates, and also peracids and precursors thereof.

Even more preferentially, the chemical oxidizing agent(s) are chosen from hydrogen peroxide, peroxygenated salts, urea peroxide or alkali metal bromates or ferricyanides.

This oxidizing agent is advantageously constituted of hydrogen peroxide, in particular in aqueous solution (aqueous hydrogen peroxide solution), the concentration of which may range more particularly from 0.1% to 50% by weight, even more preferentially from 0.5% to 20% by weight and better still from 1% to 15% by weight relative to the oxidizing composition.

Preferably, the chemical oxidizing agents are chosen from hydrogen peroxide and/or peroxygenated salts.

Preferably, the oxidizing aqueous composition also contains one or more alkaline agents, especially the alkaline agents as described previously.

The use of an oxidizing aqueous composition containing one or more alkaline agents in the course of the dyeing process according to the invention makes it possible especially to lead to a lightening effect on the treated keratin fibres, which reinforces the visibility of the pattern(s) obtained with the oxidation dyes present on the surface of the substrate.

This use is particularly advantageous for dyeing dark or chestnut-brown hair.

The oxidizing aqueous composition may also comprise one or more thickeners or viscosity regulators such as hydroxyalkylcelluloses, for instance hydroxyethylcellulose, especially sold by Ashland® under the reference Natrosol Plus 330.

The oxidizing aqueous composition may also comprise one or more colouring agents such as couplers.

In this way, placing in contact the keratin fibres, the pretreated substrate and the oxidizing aqueous composition containing one or more couplers will make it possible to lead to varied colourings, given that the coupler(s) present in the oxidizing composition will be able to react with the oxidation base(s) present on the substrate.

The use of an oxidizing aqueous composition containing one or more couplers is advantageous since it makes it possible to limit the use of the number of substrates by varying the nature of the oxidizing composition, while at the same time increasing the possible results as regards the colour.

The use of an oxidizing aqueous composition containing one or more couplers thus makes it possible to obtain a wide range of colours.

According to a preferred embodiment of the invention, the oxidizing aqueous composition also comprises one or more alkaline agents and/or one or more colouring agents such as couplers.

According to another preferred embodiment of the invention, the oxidation dyeing process comprises a step of application, to the keratin fibres, of a substrate as described previously, followed by a step of application, to the keratin fibres, of an oxidizing aqueous composition containing one or more chemical oxidizing agents.

In particular, the keratin fibres are placed on the surface of the substrate bearing the oxidation dye(s), i.e. at the place where the surface of the substrate is covered with at least one layer constituted of a dye composition comprising the oxidation dye(s), the thiolated reducing agent(s) and the organic reducing agent(s) of reductone type; and the oxidizing aqueous composition is then applied to said fibres. The oxidation dyes are thus dissolved, react with the oxidizing agent and dye the keratin fibres.

The oxidizing aqueous composition is especially applied using an applicator, in particular a brush, or by hand.

In accordance with this embodiment, after applying the oxidizing composition, the locks of hair thus treated may be protected with a paper to protect the other locks that have not been treated.

According to another embodiment, the oxidation dyeing process comprises a step of application, to the keratin fibres, of an oxidizing aqueous composition as described previously containing one or more chemical oxidizing agents, followed by a step of application, to the keratin fibres, of a substrate as defined previously.

In this embodiment, the order of application between the substrate and the oxidizing aqueous composition is thus inverted relative to the preceding embodiment.

In this embodiment, the keratin fibres are especially placed on a support, for example the upper surface of a sheet of paper, the oxidizing aqueous composition is applied to said fibres and the substrate as described previously is then applied to said fibres. The oxidation dyes present on the surface of the substrate are thus dissolved, react with the oxidizing agent and dye the covered keratin fibres.

In accordance with this embodiment, the substrate as described previously is applied to the keratin fibres treated with the oxidizing aqueous composition so that the surface containing the oxidation dye(s) is in contact with the fibres.

This dyeing process referred to hereinbelow as the "reverse dyeing process" has the advantage of minimizing or even of eliminating the problems of contamination arising between the applicator used for applying the oxidizing composition and the oxidation dyes derived from the substrate.

Specifically, when the keratin fibres are first placed on the substrate as described previously, the applicator used for applying the oxidizing composition is then in contact with the oxidation dyes originating from said substrate which react with the chemical oxidizing agents. Once the application has been performed, the applicator thus contains both oxidation dyes and the oxidizing aqueous composition, which has the consequence of entailing a risk of contamination of the rest of the oxidizing aqueous composition and of increasing the risks of impairing the colouring of the other keratin fibres.

In particular, when the applicator is a brush, its bristles contain oxidation dyes that have reacted with the oxidizing agents of the oxidizing composition. Consequently, the brush may impair the rest of the oxidizing composition, given that its bristles contain oxidation dyes.

The reverse dyeing process thus makes it possible to avoid this problem of contamination since the applicator does not come into contact with the oxidation dyes originating from said substrate. Thus, the rest of the oxidizing aqueous composition is not contaminated by the applicator and the risks of impairment of the colouring are minimized.

The reverse dyeing process is thus particularly advantageous.

Preferably, the oxidizing aqueous composition used in the reverse dyeing process also contains one or more alkaline agents.

The substrate comprising a surface coated with at least one layer constituted of a dye composition may be applied to the keratin fibres for a time ranging from 5 to 60 minutes and preferably ranging from 10 to 30 minutes.

The oxidizing aqueous composition may be applied to the keratin fibres for a time ranging from 5 to 60 minutes and preferably ranging from 10 to 30 minutes.

The substrate as described previously and the oxidizing aqueous composition may be applied at room temperature (25° C.), optionally with raising of the temperature, which may be up to 60° C.

After the treatment, the human keratin fibres are optionally rinsed with water, optionally washed with a shampoo and then rinsed with water, before being dried or left to dry.

Preferably, the substrate comprises a surface coated with at least one layer constituted of a dye composition comprising one or more oxidation dyes, one or more thiolated reducing agents, one or more organic reducing agents of reductone type, and one or more alkaline agents, and the oxidizing aqueous composition contains one or more chemical oxidizing agents and optionally one or more alkaline agents.

Process for Producing the Substrate

The present invention also relates to a process for producing the substrate as defined previously, comprising at least one step of deposition, on the surface of a substrate, of at least one dye preparation composition containing one or more oxidation dyes, one or more thiolated reducing agents, and one or more organic reducing agents of reductone type; and at least one step of drying said substrate.

It is understood, for the purposes of the invention, that the dye preparation composition used in the process for producing the substrate comprises one or more oxidation dyes, one or more thiolated reducing agents, and one or more organic reducing agents of reductone type as described previously for the dye composition.

It is also understood, for the purposes of the invention, that the dye preparation composition may optionally comprise one or more alkaline agents, one or more additional antioxidant active agents, one or more compounds capable of slowing down the oxidative condensation reaction, and/or one or more organic solvents as described previously for the compound(s) optionally present in the dye composition.

The dye preparation composition intended to be deposited on the surface of a substrate may be liquid or in pulverulent form at room temperature, preferably liquid at room temperature.

Preferably, the substrate is pretreated by at least one dye preparation composition containing one or more oxidation dyes, one or more thiolated reducing agents, one or more organic reducing agents of reductone type and one or more alkaline agents.

The oxidation base(s) and optionally the coupler(s) as described previously may advantageously represent from 0.01% to 99% by weight, preferably from 1% to 50% by weight and better still from 5% to 40% by weight relative to the total weight of the dye preparation composition before deposition on the surface of the substrate.

The thiolated reducing agent(s) as described previously are preferably present in a total amount ranging from 0.5% to 60% by weight, preferentially from 1% to 50% by weight, more particularly from 4% to 45% by weight and better still from 10% to 40% by weight relative to the total weight of the dye preparation composition before deposition on the surface of the substrate.

The organic reducing agent(s) of reductone type as described previously are preferably present in a total amount ranging from 0.5% to 50% by weight, preferentially from 1% to 45% by weight, more particularly from 4% to 35% by weight and better still from 8% to 30% by weight relative to the total weight of the dye preparation composition before deposition on the surface of the substrate.

The alkaline agent(s) may preferably be present in a content ranging from 0.01% to 20% by weight relative to the total weight of the dye preparation composition before deposition on the surface of the substrate.

The additional antioxidant active agent(s) may preferably be present in a content ranging from 0.05% to 1% by weight relative to the total weight of the dye preparation composition before deposition on the surface of the substrate.

The compound(s) capable of slowing down the oxidative condensation reaction may preferably be present in a content of less than or equal to 2% by weight, preferentially less than or equal to 1% by weight, even better still ranging from 0.05% to 0.2% by weight relative to the total weight of the dye preparation composition before deposition on the surface of the substrate.

The dye preparation composition comprising one or more oxidation dyes, one or more thiolated reducing agents, and one or more organic reducing agents of reductone type may be aqueous or anhydrous, preferably aqueous.

When said dye preparation composition is aqueous and contains one or more alkaline agents, the pH of said dye preparation composition preferably ranges from 7.5 to 13, better still from 8 to 12 and even better still from 8 to 11.

The dye composition(s) present on the surface of the substrate may optionally result from successive treatments of the substrate with one or more oxidation dyes, one or more thiolated reducing agents, and one or more organic reducing agents of reductone type on the one hand, optionally one or more alkaline agents, on the other hand, and optionally one or more active agents as described previously.

Preferably, the process for producing the substrate as described previously comprises at least one step of deposition, on the surface of a substrate, of at least one dye preparation composition containing one or more oxidation dyes, one or more thiolated reducing agents, and one or more organic reducing agents of reductone type; and at least one step of drying said substrate; more preferentially, the step(s) of deposition on the surface of a substrate consists in depositing said dye preparation composition(s) by a printing method.

In other words, the dye composition(s) are printed on the surface of a substrate, that is to say using a printing process which makes it possible to obtain the substrate defined previously.

According to this preference, the printing method which serves to deposit the dye composition(s) onto the surface of the substrate may be a screen printing process, a flexography process, an offset printing process, an inkjet printing process or a laser printing process.

Preferentially, at least one dye preparation composition as defined previously is applied to the substrate by screen printing, or by means of an inkjet printer.

More preferentially, the dye preparation composition as defined previously is printed onto the surface of the substrate by means of an inkjet printer.

When the production process consists in using a printing process using a laser printer, then the dye preparation composition containing the oxidation dye(s), the thiolated reducing agent(s), and the organic reducing agent(s) of reductone type is in powder form.

Preferably, the process for producing the substrate corresponds to a process for printing the substrate, in which at least one layer of the dye preparation composition as defined previously is applied to the substrate by screen printing, flexography, offset printing or inkjet printing.

Advantageously, in this embodiment by printing, the substrate is an element in sheet form.

This preferred production process, corresponding to a process for printing the substrate, may be carried out in the hairstyling salon itself, especially by means of the presence of an inkjet printer or a laser printer, before performing the oxidation dyeing process according to the invention.

Alternatively, this preferred process may also be performed outside the hairstyling salon and as such the user merely has to use the substrates to dye the hair.

In this case, the pretreated substrate may be supplied to the user to produce a unified colouring and/or patterns on the hair.

According to one preferred embodiment of the invention, the process for producing a substrate comprises at least one depositing step consisting in depositing at least one dye preparation composition onto the surface of the substrate covered with a layer of adhesive composition. This adhesive layer may cover all or part of the substrate. In particular, the adhesive layer may represent a pattern.

According to another preferred embodiment of the invention, the process for producing a substrate as described previously comprises at least one depositing step consisting in partially depositing onto the surface of a substrate, via a printing method, at least one dye preparation composition containing one or more oxidation dyes, one or more thiolated reducing agents and one or more organic reducing agents of reductone type.

In accordance with this other preferred embodiment, the oxidation dye(s), the thiolated reducing agent(s), and the organic reducing agent(s) of reductone type are deposited in the form of one or more patterns onto the surface of a substrate. In particular, the patterns may be squares, circles, ovals, ellipses or triangles, in the form of filled patterns or of lines surrounding these patterns. They may also be thick or thin, straight or curved lines, crossed lines, representing letters, stylized drawings or geometrical patterns. They may also be dotted lines or spots.

According to one embodiment of the invention, the process for producing the substrate comprises at least one step of deposition, on the surface of a substrate, of at least one dye preparation composition containing the oxidation dye(s), the thiolated reducing agent(s), and the organic reducing agent(s) of reductone type, then a step of heating said surface. Preferably, the surface of the substrate is partially heated so as to create one or more patterns on the surface.

According to another embodiment of the invention, the process for producing the substrate comprises at least one step of deposition of at least one dye preparation composition containing the oxidation dye(s), the thiolated reducing agent(s), and the organic reducing agent(s) of reductone type on the surface of a substrate, then a step of removing or inactivating, in some areas, all or part of the oxidation dyes. In this way, this process can lead to the production of one or more patterns on the surface of the substrate.

The step of removing all or part of the oxidation dyes in some areas may be performed by means of scraping, sponging, blowing, sucking or using an adhesive surface or a surface that is wetted at the places where it is desired to remove the oxidation dye(s).

The step of inactivating all or part of the oxidation dyes in some areas on the surface of the substrate may be performed by means of a chemical transformation, for example an oxidation or a reduction, or by covering with a protective compound.

Moreover, the process for producing the substrate may also comprise a step that consists in applying a film of starch so as to reinforce the solidity of the substrate and improve the deposition of the oxidation dye(s) onto the surface of the substrate.

The film of starch may be thin, of the order of 2 $g/m^2$, or thick, of the order of 70 $g/m^2$.

Once the dye preparation composition(s) have been deposited at the surface of the substrate, the substrate is then dried.

The substrate thus pretreated in accordance with the production process preferably dries within a period ranging from 5 minutes to 120 minutes, preferentially from 5 minutes to 90 minutes, more preferentially from 1 minute to 60 minutes and better still from 5 minutes to 60 minutes.

Preferably, the step of drying said substrate consists in leaving said substrate to dry in the open air.

Once the substrate has been prepared, it comprises a surface coated with at least one layer constituted of a dye composition comprising one or more oxidation dyes, one or more thiolated reducing agents, and one or more organic reducing agents of reductone type.

For the purposes of the present invention, the dye composition(s) have a total water content of less than 20% by weight, preferably less than or equal to 15% by weight, more preferentially less than or equal to 10% by weight, relative to the total weight of the dye composition.

The oxidation base(s) and optionally the coupler(s) as described previously may advantageously represent from 0.01% to 99% by weight, preferably from 1% to 50% by weight and better still from 5% to 40% by weight relative to the total weight of the dye composition.

Preferably, the dye composition comprises one or more oxidation dyes as described previously in a content ranging from 0.01% to 99% by weight, preferably from 1% to 50% by weight and better still from 5% to 40% by weight relative to the total weight of the dye composition.

The thiolated reducing agent(s) as described previously are preferably present in a total amount ranging from 0.5% to 60% by weight, preferentially from 1% to 50% by weight, more particularly from 4% to 45% by weight and better still from 10% to 40% by weight relative to the total weight of the dye composition.

The organic reducing agent(s) of reductone type as described previously are preferably present in a total amount ranging from 0.5% to 50% by weight, preferentially from 1% to 45% by weight, more particularly from 4% to 35% by weight and better still from 8% to 30% by weight relative to the total weight of the dye composition.

The alkaline agent(s) as described previously may preferably be present in a content ranging from 0.01% to 20% by weight relative to the total weight of the dye composition.

The additional antioxidant active agent(s) may preferably be present in a content ranging from 0.5% to 10% by weight relative to the total weight of the dye composition.

The compound(s) capable of slowing down the oxidative condensation reaction as described previously may preferably be present in a content of less than or equal to 10% by weight, preferentially less than or equal to 5% by weight, even better still ranging from 0.5% to 2% by weight relative to the total weight of the dye composition.

The invention also relates to an element in sheet form as described previously, pretreated at the surface thereof by a dye preparation composition comprising one or more oxidation dyes, one or more thiolated reducing agents, and one or more organic reducing agents of reductone type, as described previously.

The element in sheet form is therefore entirely or partially covered at the surface thereof by one or more oxidation dyes, one or more thiolated reducing agents, and one or more organic reducing agents of reductone type.

The element in sheet form comprises, at the surface thereof, one or more oxidation dyes, one or more thiolated reducing agents, and one or more organic reducing agents of reductone type.

In particular, the oxidation dye(s), the thiolated reducing agent(s) and the organic reducing agent(s) of reductone type have been printed on the element in sheet form.

The element in sheet form may be made from a nonwoven fibre material, especially a nonwoven made of cellulose or a derivative thereof. In particular, the element in sheet form may be a paper of kraft type, which has the advantage of printing well and of leading to precise patterns. Specifically, the coloured patterns obtained on the keratin fibres do not run following the application of the oxidizing aqueous composition.

The element in sheet form may be a sheet of plastic material which especially has the advantage of rendering well the colouring power, which makes it possible to lead to patterns whose colouring is powerful. Furthermore, the sheet of plastic material does not absorb the water present in the oxidizing aqueous composition, which makes it possible to avoid creating dry areas under the keratin fibres during the application of said composition.

According to a first advantageous embodiment, the element in sheet form is a plastic sheet covered with a thin layer of paper, in particular with a thickness of less than 50 µm and more preferentially less than 30 µm, such as cigarette paper or a layer of paper that can be broken down in the presence of water, such as toilet paper, or a thin layer of hydrophilic material, preferably dissolved, such as cellulose or a hydrophilic silica, preferably having a thickness ranging from 5 to 200 µm.

In accordance with this embodiment, the layer of thin paper allows rapid drying and prevents the colouring from running following the application of the oxidizing aqueous composition. Furthermore, the layer of paper located below the thin paper absorbs little or none of the oxidation dye(s) derived from the element in sheet form, as a result of its low thickness. The colouring is thus rendered well by the layer of thin paper on the keratin fibres, which leads especially to sharp coloured patterns. Furthermore, the element in sheet form in accordance with this embodiment makes it possible to minimize the dry areas under the keratin fibres.

When use is made of a support formed from a layer of paper, which is preferentially sparingly absorbent or non-absorbent, covered with a layer of paper that is capable of degrading on contact with water:

the layer of degradable paper (thickness possibly ranging from 10 to 200 µm) allows rapid drying and prevents the colouring from running following the application of the oxidizing aqueous composition. Furthermore, the layer of paper located below the degradable paper absorbs little or none of the oxidation dye(s) derived from the element in sheet form, as a result of its low thickness. The colouring is thus rendered well by the layer of thin paper on the keratin fibres, which leads especially to sharp coloured patterns. Furthermore, the element in sheet form in accordance with this embodiment makes it possible to minimize the dry areas under the keratin fibres.

In the case where a support formed from a layer of hydrophilic material is used:

the layer of hydrophilic material is typically from 5 to 200 µm thick, which allows rapid drying and prevents the colouring from running following the application of the oxidizing aqueous composition. This especially results in sharp coloured patterns.

According to a second advantageous embodiment, the element in sheet form is a microalveolar sheet, i.e. a sheet perforated with holes that are spaced apart from each other by a plastic material. Thus, the oxidizing aqueous composition becomes housed in the holes of the substrate, which will make it possible to better render the power of the dyes on the keratin fibres after application of the oxidizing aqueous composition.

The holes are located at the surface of the element in sheet form over a thickness ranging from 10% to 90% of the thickness of the sheet.

In accordance with this embodiment, the element in sheet form also has the advantage of printing well, of better rendering the colouring leading especially to powerfully coloured patterns, of not excessively absorbing the water originating from the oxidizing aqueous composition and of minimizing the risks of running of the colouring, which results in precisely coloured patterns on the keratin fibres.

The examples that follow serve to illustrate the invention without, however, being limiting in nature.

EXAMPLES

A dye preparation composition C1 for treating the surface of the substrate according to the invention is prepared from the ingredients shown in the table below, the amounts of which are expressed as weight percentages of active material (AM).

| Ingredients | Composition C1 |
| --- | --- |
| 2,5-Toluenediamine | 4 |
| 4-(2-hydroxyethoxy)-1,3-phenylenediamine dihydrochloride | 7.9 |
| (C14/C16) alkyl hydroxyethylcellulose | 1 |
| Erythorbic acid | 3 |
| Thiolactic acid | 4 |
| Water | qs 100 |

Preparation of a Substrate S1:

840 mg of Composition C1 are Applied Uniformly Using a HandCoater (Sold by RK PrintCoat Instruments Ltd., K-HandCoater range, under the reference "yellow") on a 20×10 cm substrate of parchment paper type. The deposit of dye preparation composition C1 is thus 4.2 mg/cm$^2$ before drying.

The substrate S1 is then dried. Once the substrate S1 is dry, the layer constituted of the dry composition C1 on the surface of the substrate S1 has the following amounts of ingredients (expressed as weight percentage of active material):

| Ingredients | Amounts (% AM) |
| --- | --- |
| 2,5-Toluenediamine | 20 |
| 4-(2-hydroxyethoxy)-1,3-phenylenediamine dihydrochloride | 40 |
| (C14/C16) alkyl hydroxyethylcellulose | 5 |
| Erythorbic acid | 15 |
| Thiolactic acid | 20 |

Preparation of the Oxidizing Composition:

The oxidizing composition is an Oxydant Crème L'Oréal "2" 30 V, equivalent to 9 volumes of hydrogen peroxide.

Example 1

A first substrate S1 is prepared, then is used according to the following oxidation dyeing process:

1) 1.5 g of grey hair containing 90% white hair are deposited on the surface treated by the dye preparation composition C1 of the substrate S1; then 2) the oxidizing composition is applied to the lock of hair deposited on SC1, then
3) the lock is left to stand for 30 minutes, and finally
4) the lock is rinsed, washed with a shampoo and rinsed with water.

A second substrate S1 is prepared, it is then placed in a bag, placed under vacuum, and finally placed under an inert atmosphere by filling with argon.

The bag is then stored at atmospheric pressure and ambient temperature for 6 weeks.

The bag is then opened and this second substrate S1 is used according to the same oxidation dyeing process as described above.

After drying the locks of hair, it is observed that the locks of hair treated with the first or the second substrate S1 have an intense midnight blue colour that is judged to be satisfactory.

Example 2

14 different dye compositions CT1 to CT14 are prepared, each comprising 2,5-toluenediamine, 4-(2-hydroxyethoxy)-1,3-phenylenediamine dihydrochloride, (C14/C16) alkyl hydroxyethylcellulose, water, and one or more compounds chosen from erythorbic acid, thiolactic acid, sodium bisulfite, ethylenediaminetetraacetic acid (EDTA) and mixtures thereof.

840 mg of each dye preparation composition CT1 to CT14 are applied uniformly using a HandCoater (sold by RK PrintCoat Instruments Ltd., K-HandCoater range, under the reference "yellow") on a different 20×10 cm substrate of parchment paper type. The deposit of each dye preparation composition CT1 to CT14 is thus 4.2 mg/cm$^2$ before drying.

In other words, each substrate is treated at the surface thereof by a single dye preparation composition.

The 14 substrates prepared in this way are then dried, then placed in bags independently of one another, placed under vacuum, and finally placed under an inert atmosphere by filling with argon.

The 14 bags are then stored at atmospheric pressure and ambient temperature for 4 weeks.

The preservation of the 14 substrates is then evaluated just after opening the bag, and 3 days after opening.

The amounts (expressed as weight percentages of active material) of the ingredients present in the layers constituted of the dry dye compositions CT1 to CT14, and also the results of the evaluations of stability of the 14 substrates, are collated in the tables below:

|  |  | Amounts in the layers constituted of the dry dye compositions CT1 to CT4 (as % AM) | | | |
|---|---|---|---|---|---|
|  |  | CT1 (Invention) | CT2 (Invention) | CT3 (Invention) | CT4 (Invention) |
| Ingredients | 2,5-Toluenediamine | 21.9 | 22.1 | 21.7 | 21.9 |
|  | 4-(2-hydroxyethoxy)-1,3-phenylenediamine dihydrochloride | 43.8 | 44.3 | 43.3 | 43.8 |
|  | (C14/C16) alkyl hydroxyethylcellulose | 5.5 | 5.6 | 5.4 | 5.5 |
|  | Sodium bisulfite | 0.8 |  | 0.8 |  |
|  | Erythorbic acid | 12 | 12 | 12 | 12 |
|  | Thiolactic acid | 16 | 16 | 16 | 16 |
|  | EDTA |  |  | 0.8 | 0.8 |
| Stability to oxidation from the air |  | ++ | ++ | + | + |

|  |  | Amounts in the layers constituted of the dry dye compositions CT5 to CT8 (as % AM) | | | |
|---|---|---|---|---|---|
|  |  | CT5 (Outside the invention) | CT6 (Outside the invention) | CT7 (Outside the invention) | CT8 (Outside the invention) |
| Ingredients | 2,5-Toluenediamine | 27.1 | 26.6 | 26.8 | 25.3 |
|  | 4-(2-hydroxyethoxy)-1,3-phenylenediamine dihydrochloride | 54.2 | 53.2 | 53.7 | 50.7 |
|  | (C14/C16) alkyl hydroxyethylcellulose | 6.7 | 6.6 | 6.7 | 6.4 |
|  | Sodium bisulfite |  | 0.8 | 0.8 | 0.8 |
|  | Erythorbic acid | 12 | 12 | 12 |  |
|  | Thiolactic acid |  |  |  | 16 |
|  | EDTA |  | 0.8 |  | 0.8 |
| Stability to oxidation from the air |  | − | − | − | −− |

|  |  | Amounts in the layers constituted of the dry dye compositions CT9 to CT12 (as % AM) | | | |
|---|---|---|---|---|---|
|  |  | CT9 (Outside the invention) | CT10 (Outside the invention) | CT11 (Outside the invention) | CT12 (Outside the invention) |
| Ingredients | 2,5-Toluenediamine | 25.7 | 25.8 | 30.5 | 30.5 |
|  | 4-(2-hydroxyethoxy)-1,3-phenylenediamine dihydrochloride | 51.3 | 51.7 | 61.1 | 61.1 |

| | Amounts in the layers constituted of the dry dye compositions CT9 to CT12 (as % AM) | | | |
|---|---|---|---|---|
| | CT9 (Outside the invention) | CT10 (Outside the invention) | CT11 (Outside the invention) | CT12 (Outside the invention) |
| (C14/C16) alkyl hydroxyethylcellulose | 6.2 | 6.5 | 7.6 | 7.6 |
| Sodium bisulfite | 0.8 | | 0.8 | |
| Erythorbic acid | | 16 | | |
| Thiolactic acid | 16 | | | |
| EDTA | | | | 0.8 |
| Stability to oxidation from the air | -- | -- | -- | -- |

| | | Amounts in the layers constituted of the dry dye compositions CT13 to CT14 (as % AM) | |
|---|---|---|---|
| | | CT13 (Outside the invention) | CT14 (Outside the invention) |
| Ingredients | 2,5-Toluene-diamine | 26.8 | 25.7 |
| | 4-(2-hydroxy-ethoxy)-1,3-phenylenediamine dihydrochloride | 53.7 | 51.3 |
| | (C14/C16) alkyl hydroxyethyl-cellulose | 6.7 | 6.2 |
| | Sodium bisulfite | | |
| | Erythorbic acid | 12 | |
| | Thiolactic acid | | 16 |
| | EDTA | 0.8 | 0.8 |
| Stability to oxidation from the air | | -- | -- |

The evaluation of the stability of the substrates to atmospheric oxygen was graded as follows:
++: Satisfactory substrate upon opening the bag and 3 days after opening
+: Satisfactory substrate upon opening the bag
−: Unsatisfactory substrate upon opening the bag
−−: Particularly unsatisfactory substrate upon opening the bag It is observed that the substrates according to the invention have better stability over time to atmospheric oxygen than the substrates outside the invention.

Example 3

A plastic mask is produced containing square holes 1 cm×1 cm, forming a chequerboard.

The same tests as in example 1 are carried out with the composition C1 and the comparative compositions CT5 to CT14.

The compositions are applied using a HandCoater (sold by RK PrintCoat Instruments Ltd., K-HandCoater range, under the reference "yellow") on a substrate of parchment paper type (virtually the whole sheet is covered). The deposit is 660 mg for the whole sheet, i.e. a deposit of 6.6 mg/cm$^2$ of squares of the sheet covered.

It is observed that the performance is unacceptable in the case of the tests using the compositions outside the invention and in which the bag is opened after storage for one month. With the tests using the composition C1, the result is identical between the test in which the bag was opened after storage for one month and the result obtained with the freshly produced sheet.

The invention claimed is:

1. Process for the oxidation dyeing of keratin fibres, comprising:
   i) a step of application, to said keratin fibres, of a substrate comprising a surface coated with at least one layer constituted of a dye composition comprising:
      one or more oxidation dyes;
      one or more thiolated reducing agents, and
      one or more organic reducing agents of reductone type; and
   ii) a step of application, to said keratin fibres, of an oxidizing aqueous composition comprising one or more chemical oxidizing agents;
   it being understood that the total water content of said dye composition is less than 20% by weight relative to the total weight of the dye composition.

2. Process according to claim 1, characterized in that the substrate is an element in sheet form.

3. Process according to claim 2, characterized in that the element in sheet form is made of plastic material, paper, metal, a woven, a nonwoven of non-absorbent fibres, or polyamide 6,6.

4. Process according to claim 2, characterized in that the element in sheet form comprises an adhesive layer on which are deposited one or more oxidation dyes, one or more thiolated reducing agents and one or more organic reducing agents of reductone type.

5. Process according to claim 1, characterized in that the oxidation dyes are chosen from oxidation bases and couplers.

6. Process according to claim 5, characterized in that the oxidation bases are chosen from para-phenylenediamines, bisphenylalkylenediamines, para-aminophenols, ortho-aminophenols and heterocyclic bases, the addition salts thereof, and mixtures thereof.

7. Process according to claim 5, characterized in that the couplers are chosen from meta-phenylenediamines, meta-aminophenols, meta-diphenols, naphthalene-based couplers and heterocyclic couplers, the addition salts thereof, and mixtures thereof.

8. Process according to claim 1, characterized in that the thiolated reducing agent(s) are chosen from those of formula i-1, the organic or mineral acid or base salts thereof, optical isomers thereof, tautomers thereof, and the solvates; and/or the mixtures thereof:

$$R\text{—}SH \qquad \text{i-1}$$

in which formula i-1:
R represents:
   a linear or branched $(C_1\text{-}C_8)$alkyl, which is optionally substituted with one or more groups chosen from carboxy C(O)OH, (di)($C_1$-$C_4$)(alkyl)amino, hydroxyl —OH, thiol —SH; and/or optionally interrupted with one or more heteroatoms or groups chosen from —O—, —S—, —N(R''')—, C(O) or combinations thereof; with R''' representing a hydrogen atom or a ($C_1$-$C_6$)alkyl group; or a (hetero)aryl group optionally substituted with one or more hydroxyl, thiol or carboxy groups.

9. Process according to claim 1, characterized in that the thiolated reducing agent(s) are chosen from those of formula i 1 the organic or mineral acid or base salts thereof, optical isomers thereof tautomers thereof, the solvates; and/or the mixtures thereof, for which R represents a linear or branched ($C_1$-$C_8$)alkyl,
which is substituted with one or more groups chosen from carboxy C(O)OH, amino, hydroxyl —OH and thiol —SH; and/or
which is optionally interrupted with one or more heteroatoms or groups chosen from —O—, —N(R''')—, C(O) or combinations thereof, with R''' representing a hydrogen atom or a ($C_1$-$C_6$)alkyl group.

10. Process according to claim 8, characterized in that the thiolated reducing agent(s) are chosen from those of formula i-1, and also the organic or mineral acid or base salts thereof, optical isomers thereof tautomers thereof, the solvates; and/or the mixtures thereof, for which R represents:
a phenyl group optionally substituted with one or more hydroxyl, thiol or carboxy groups; or
a 5- to 10-membered, heteroaryl, comprising from 1 to 4 heteroatoms chosen from O, S or N, optionally substituted with one or more hydroxyl or thiol groups.

11. Process according to claim 1, characterized in that the thiolated reducing agent(s) are chosen from thioglycolic acid, thiolactic acid, cysteine, cysteamine, homocysteine, glutathione, thioglycerol, thiomalic acid, 2-mercaptopropionic acid, 3-mercaptopropionic acid, thiodiglycol, 2-mercaptoethanol, dithiothreitol, N-acetylcysteine, esters and amides of thioglycolic or thiolactic acids, the organic or mineral acid or base salts thereof, optical isomers thereof tautomers thereof, the solvates and mixtures of these compounds.

12. Process according to claim 1, characterized in that the thiolated reducing agent(s) are present in a total amount ranging from 0.5% to 60% by weight, relative to the total weight of the dye composition.

13. Process according to claim 1, characterized in that the organic reducing agent(s) of reductone type are chosen from those of general formula (IX) the salts thereof; and/or the mixtures thereof:

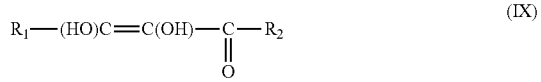

in which formula
$R_1$ and $R_2$ independently of one another each denote a group containing at least one carbon and/or oxygen atom, $R_1$ and $R_2$ possibly forming with the three carbon atoms of the compound of formula (IX) a 5- or 6-membered ring, the additional constituent atoms of which are constituted of carbon and/or oxygen atoms.

14. Process according to claim 1, characterized in that the organic reducing agent(s) of reductone type are chosen from those of formula (IX) the salts thereof and/or the mixtures thereof, for which R1 and R2 form, with the three carbon atoms of the compound of formula (IX), a 5-membered ring, the additional constituent atoms of which are constituted of carbon and/or oxygen atoms.

15. Process according to claim 1, characterized in that the organic reducing agent(s) of reductone type are chosen from reductic acid, ascorbic acid, erythorbic acid or isoascorbic acid, salts thereof, ascorbyl palmitate, and/or mixtures thereof.

16. Process according to claim 1, characterized in that the organic reducing agent(s) of reductone type are present in a total amount ranging from 0.5% to 50% by weight, relative to the total weight of the dye composition.

17. Process according to claim 1, characterized in that the dye composition comprising the oxidation dye(s), the thiolated reducing agent(s) and the organic reducing agent(s) of reductone type is present over part of the surface of the substrate and represents patterns.

18. Process according to claim 17, characterized in that the substrate comprises, on the face opposite the face bearing the oxidation dye(s), the thiolated reducing agent(s) and the organic reducing agent(s) of reductone type, a copy of the patterns.

19. Process according to claim 1, characterized in that the surface of the substrate comprises, prior to the deposition of the oxidation dye(s), the thiolated reducing agent(s) and the organic reducing agent(s) of reductone type, one or more patterns.

20. Process according to claim 1, characterized in that the substrate is transparent.

21. Process according to claim 1, characterized in that the substrate also comprises on its surface one or more alkaline agents.

22. Process according to claim 1, characterized in that the substrate also comprises, on its surface, one or more additional antioxidant active agents.

23. Process according to claim 1, characterized in that the oxidizing aqueous composition comprises one or more chemical oxidizing agents chosen from hydrogen peroxide and/or peroxygenated salts.

24. Process according to claim 1, characterized in that the oxidizing aqueous composition also comprises one or more alkaline agents and/or one or more colouring agents.

25. Process according to claim 1, characterized in that it consists in applying said oxidizing aqueous composition to keratin fibres, then in applying, to said fibres, said substrate.

26. Process for producing the substrate as defined according to claim 1, characterized in that it comprises at least one step of deposition, on the surface of a substrate, of at least one dye preparation composition containing one or more oxidation dyes, one or more thiolated reducing agents, and one or more organic reducing agents of reductone type; and at least one step of drying said substrate.

27. Process according to claim 26, characterized in that the printing method is a screen printing process, a flexography process, an offset printing process, an inkjet printing process or a laser printing process.

28. Element in sheet form, pretreated at the surface thereof by a dye preparation composition comprising one or more oxidation dyes, one or more thiolated reducing agents, and one or more organic reducing agents of reductone type; said oxidation dye(s), thiolated reducing agent(s) and organic reducing agent(s) of reductone type being printed on the said element in sheet form.

29. Element in sheet form according to claim 28, characterized in that it is chosen from a plastic sheet covered with a layer of paper having a thickness of less than 50 μm or a layer of hydrophilic material having a thickness ranging from 5 to 200 μm.

30. Element in sheet form according to claim 28, characterized in that it is chosen from a microalveolar sheet in which the holes are spaced apart from each other by a plastic material.

* * * * *